United States Patent [19]

Hills

[11] 3,947,423

[45] Mar. 30, 1976

[54] POLYESTERS CONTAINING BICYCLIC PHOSPHATE FLAME RETARDANT

[75] Inventor: William A. Hills, Trenton, N.J.

[73] Assignee: FMC Corporation, Philadelphia, Pa.

[22] Filed: May 13, 1974

[21] Appl. No.: 469,097

Related U.S. Application Data

[62] Division of Ser. No. 368,732, June 11, 1973, Pat. No. 3,849,522.

[52] U.S. Cl............ 260/45.8 R; 260/75 H; 264/211
[51] Int. Cl.² ............................................ C08J 3/20
[58] Field of Search......... 260/45.8 R, 927 R, 75 H; 264/211

[56] References Cited
UNITED STATES PATENTS

| | | | |
|---|---|---|---|
| 3,293,327 | 12/1966 | Hechenbleikner et al. | 260/936 |
| 3,427,267 | 2/1969 | Stieger et al. | 260/75 |
| 3,454,672 | 7/1969 | Jackson | 260/75 |
| 3,658,634 | 4/1972 | Yanagi et al. | 260/45.7 |
| 3,808,296 | 4/1974 | Brunetti | 260/927 |
| 3,849,368 | 11/1974 | Anderson et al. | 260/45.8 |

*Primary Examiner*—V. P. Hoke

[57] ABSTRACT

A novel compound, bis((1-oxo-2,6,7-trioxa-1-phosphabicyclo[2.2.2]oct-4-yl)methyl) 2,5-dibromoterephthalate, which is a highly effective flame-retardant additive for polyesters, and flame-retardant polyester compositions containing it.

5 Claims, No Drawings

POLYESTERS CONTAINING BICYCLIC PHOSPHATE FLAME RETARDANT

This is a division of application Ser. No. 368,732, filed June 11, 1973, now U.S. Pat. No. 3,849,522.

This invention relates to flame-retardant polyester compositions. More particularly, the invention relates to flame-retardant polyester fibers, films and molded articles wherein the flame-retardant additive is a novel phosphate-containing ester of 2,5-dibromoterephthalic acid.

Polyester compositions containing organic phosphorus and organic halogen compounds are known and are disclosed, for example, in U.S. Pat. Nos. 3,356,631, issued Dec. 5, 1971, to Jackson et al.; 3,645,962, issued Feb. 29, 1972, to Schwarz; 3,681,281, issued Aug. 1, 1972, to Juelke et al.; 3,688,001, issued Aug. 29, 1972, to Exner et al.; 3,708,328, issued Jan. 2, 1973, to Kelkheim et al.; and West German Pat. No. 2,001,125 (1970) to Caldwell et al. (Eastman Kodak Company). The aforesaid patents deal with methods and additives for imparting flame retardance to polyesters.

However, it has always been desirable to provide more efficient flame retardants which are thermally stable and which can be incorporated into molten polyester prior to formation of fibers, film or molded articles.

According to the present invention, there has been discovered a novel compound, bis((1-oxo-2,6,7-trioxa-1-phosphabicyclo[2.2.2]oct-4-yl)methyl) 2,5-dibromoterephthalate, which is a highly effective flame retardant for polyesters and is particularly suited for use in connection with polyester fibers.

The novel compound of the present invention is represented by the following formula:

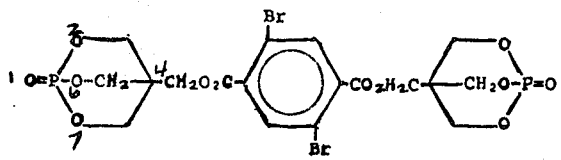

and may be prepared by reacting 4-hydroxymethyl-2,6,7-trioxa-1-phosphabicyclo[2.2.2]octane and 2,5-dibromo-terephthaloyl chloride in acetonitrile solvent utilizing pyridine as a catalyst.

A further embodiment of the present invention resides in polyester fibers, films and molded articles containing from about 5 to 25% by weight, based on the combined weight of polyester and flame retardant, of the novel compound of the present invention.

The polyesters which are rendered flame-retardant in accordance with the present invention include both the fiber- and film-forming linear saturated polyesters derived from saturated aliphatic and aromatic dicarboxylic acids and saturated diols and linear unsaturated polyesters which are principally employed for casting and molding applications.

The fiber- and film-forming saturated polyesters are prepared from dicarboxylic acids such as terephthalic acid, isophthalic acid, adipic acid, diphenyl-4,4'-dicarboxylic acid (bibenzoic acid), 4,4'-di(carboxyphenyl)methane, 2,6-naphthalene-dicarboxylic acid, 1,3-cyclopentanedicarboxylic acid, 1,3-cyclohexanedicarboxylic acid and the like. Diols generally employed to prepare the fiber- and film-forming polyesters are the saturated aliphatic, saturated cycloaliphatic or aromatic diols, preferably the lower alkane diols such as ethylene glycol, propylene glycol and butylene glycol. Other exemplary diols include ethylene diglycol, dimethylolcyclohexane, 1,6-hexanediol, p-xylylenediol and the like. Particularly preferred are fiber- and film-forming polyesters prepared from ethylene glycol and terephthalic acid. These fiber- and film-forming polyesters generally have an average molecular weight of at least about 10,000.

Unsaturated polyesters are characterized in that they are based on macromolecules with a polyester backbone in which both a saturated acid, e.g., phthalic, isophthalic or adipic acid, and an unsaturated acid such as maleic or fumaric acid are condensed with a diol. A three dimensional structure is obtained by cross-linking the linear polyester backbone through the unsaturated acid component with a vinyl monomer, which is usually styrene. Conventional peroxide initiators are employed, such as benzoyl peroxide or cumene hydroperoxide. The cross-linking monomers also may act as solvents for the polyester so as to produce a liquid, low viscosity polyester-monomer system which is useful for casting and molding applications. Before addition of the vinyl monomer, the polyester backbone usually has a molecular weight of about 1,000 to 5,000.

A particularly preferred embodiment of the present invention resides in providing flame-retardant spun polyester fibers such as polyethylene terephthalate, poly(1,4-cyclohexylenedimethylene)terephthalate or polyethylene 2,6-naphthalenedicarboxylate spun fibers having significantly improved flame-retardant characteristics.

As is known in the art, polyester fibers are conventionally prepared by the so-called melt spinning technique. In this method, the molten polyester is extruded under pressure through a spinneret plate having a plurality of small circular openings about 0.009 inch in diameter. The spinning is carried out at a temperature of from about 260° to 300°C for polyethylene terephthalate fibers. The polymeric polyester has been previously prepared either by the batch method or by the continuous polymerization technique.

Thus, in view of the conditions employed in the melt spinning process, there are a significant number of problems to be overcome in successfully incorporating an effective flame retardant during melt spinning. The flame retardant must be thermally stable, it must be both unreactive with and soluble in the molten polyester. In addition, the flame retardant must have a low volatility at spinning temperatures and should not in any way interfere with the operation of the spinneret. The flame retardant should also have no substantial adverse effect upon the physical properties of the spun fiber.

The novel flame-retardant compound of the present invention, bis((1-oxo-2,6,7-trioxa-1-phosphabicyclo[2.2.2]oct-4-yl)methyl) 2,5-dibromoterephthalate meets all these important criteria and is particularly suitable for use in connection with the melt spinning process for producing polyester fibers.

Generally speaking, from about 5 to 25% of the novel flame-retardant compound of the present invention is employed based on the combined weight of polyester and additive, i.e., 5 to 25 parts by weight of flame retardant and 75 to 95 parts by weight of polyester. Preferably about 10 to 22% by weight of the novel flame-retardant additive is employed.

Flame-retardant polyester fibers prepared in accordance with the present invention may be used as such or may be blended with other fibrous materials such as cotton, rayon, nylon, acetate, acrylics and the like, and such blends are well known to those in the textile art.

Polyesters useful for molding compositions will generally contain inorganic reinforcing fillers such as mineral silicates, silica gel, asbestos, clay, talc, and the like which improve the physical properties of the molding compounds, with glass fibers being a preferred reinforcing additive for such compositions at concentrations of about 10 to 50% by weight of the total molding composition.

Of course, flame-retardant polyester fibers, films and molded articles prepared in accordance with the present invention may contain a wide variety of additional ingredients such as plasticizers, dyes, heat and color stabilizers, pigments, antioxidants, antistatic agents and various other special purpose additives employed in the processing of polyester compositions.

The invention is further illustrated by the following examples which are not to be considered as limitative of its scope. All parts and percentages are by weight of (based on) the total weight of the composition and temperatures are in degrees centigrade, unless otherwise stated.

EXAMPLE I

A mixture of 72 g (0.4 mole) of 4-hydroxymethyl-2,6,7-trioxa-1-phosphabicyclo[2.2.2]octane and 72 g (0.2 mole) 2,5-dibromoterephthaloyl choride and 400 ml of acetonitrile containing 7 drops of pyridine was placed in a 1 liter flask equipped with a magnetic stirrer, reflux condenser and drying tube, and was heated under a gentle reflux until the evolution of hydrochloride gas stopped. A solid precipitated from the reaction mixture as the reaction proceeded. The mixture was filtered and 127 g of white solid was collected. The solid was washed several times with 10% sodium carbonate solution, then with distilled water and dried to give 103.3 g of white solid identified as bis((1-oxo-2,6,7-trioxa-1-phosphabicyclo[2.2.2]oct-4-yl)methyl) 2,5-dibromoterephthalate having a melting point >310°C.

EXAMPLE II

The flame retardancies of polyethylene terephthalate (PET) plaques containing the compound prepared in Example I were determined by measuring the Limiting Oxygen Index (LOI) of the plaques.

The plaques were first prepared as follows:

One brass plate (6×6 inches chrome plated) is placed on the bottom (chrome side up), a 6×6×¼ inch spacer (1/32 inch stainless steel) is placed on a 6½×6½ inch sheet of aluminum foil and the edges are folded over and pressed into place. This is then placed on the brass plate. A 6 gram 10-mesh screened sample of ground polymer (containing the flame-retardant additive) is spread evenly on the foil in the 5½×5½ inch square framed by the spacer. A fiberglass fabric (5½×5½ inch) is placed over the polymer. A second 6 gram portion of the polymer-additive composition is spread evenly over the fiberglass fabric. A 6×6 inch sheet of aluminum foil is placed over the polymer and a second chrome plated brass plate is put on top (chrome side in). The mold assembly is placed in a hydraulic press previously heated to 275°C, the plates are closed gently and to allow melting (about 3 minutes) then the pressure is increased rapidly to 10,000–12,000 pounds. After one minute the pressure is released and the mold quenched in a cold water bath. The foil is removed and the composite cut out. The 5½ inch square plastic composite of PET resin and glass fabric is cut into 3½×½ inch strips which are dried at 100°C for one hour.

The LOI test is made by supporting the 3½×½ inch sample strip in a U-shaped frame which is mounted in a cylindrical open chamber. Controlled mixtures of oxygen and nitrogen gases are admitted into the base of the chamber and allowed to displace the normal atmosphere. When an equilibrium atmosphere in the chamber is obtained, the sample is ignited with a butane gas flame by contacting the flame to the top edge of the sample. If it fails to ignite, the oxygen ratio of the atmosphere is increased to a level where the flame will just propagate. Conversely, if the sample strip ignites and the flame propagates, the oxygen ratio of the atmosphere is reduced to a level where flame propagation is virtually zero. The LOI is the minimum percentage concentration of the oxygen atmosphere in which the test sample will ignite and permit flame propagation.

The LOI test was introduced in 1966 (Fennimore et al., Modern Plastics, 43, 141 (1966) and is the basis for ASTM-D-2863-70. The apparatus used was the Oxygen Index Flammability Tester (Model JD14) manufactured by MKM Machine Tool Co., Inc.

The LOI results for PET plaques containing various amounts of the novel additive prepared in Example I are set forth in the table below:

TABLE I

| Sample | Flammability Data % Additive of Example I | LOI |
|---|---|---|
| 1 | none | 21.0 |
| 2 | 10.5 | 29.2 |
| 3 | 21.0 | 37.2 |

EXAMPLE III

Twenty parts of the novel compound of Example I was mix-melted with 80 parts of polyethylene terephthalate under $N_2$ and the admixture was observed using a hot stage microscope. The sample melted without decomposition at 249°–252°C and became fluid; decomposition did not take place. The temperature was raised to 285°C and held there for 10 minutes, and then to 290°C and maintained at 290°C for an additional 10 minutes. No visible increase in viscosity was observed nor was there observed any darkening or other evidence of decomposition. This example demonstrates the thermal stability of the blend.

What is claimed is:

1. A flame-retardant polyester composition comprising a linear saturated, fiber-forming polyester and from 5 to 25% by weight of bis-((1-oxo-2,6,7-trioxa-1-phosphabicyclo[2.2.2]-oct-4-yl)methyl)2,5-dibromoterephthalate as the flame retardant additive, based on the combined weight of polyester and said flame-retardant additive.

2. The composition of claim 1 where there is present from 10 to 22% by weight of the flame-retardant additive, based on the combined weight of said polyester and said flame-retardant additive.

3. A fiber formed from the composition of claim 1.

4. The composition of claim 3 wherein the polyester is a member of the group consisting of polyethylene terephthalate, poly(1,4-cyclohexylenedimethylene)-terephthalate and polyethylene 2,6-naphthalenedicarboxylate.

5. A process for preparing the flame-retardant polyester fiber of claim 4 which comprises admixing the flame-retardant additive with molten polyester and thereafter extruding the admixture at elevated temperatures through a spinneret plate whereby a spun, flame-retardant polyester fiber is produced.

* * * * *